US00PP12803P2

(12) United States Plant Patent
Ballantyne

(10) Patent No.: US PP12,803 P2
(45) Date of Patent: Jul. 23, 2002

(54) ***ATHYRIUM NIPONICUM* VAR *PICTUM* PLANT NAMED 'SILVER FALLS'**

(76) Inventor: Diana Ballantyne, P.O. Box 478, Boring, OR (US) 97009

( * ) Notice: Subject to any disclaimer, the term of this patent is extended or adjusted under 35 U.S.C. 154(b) by 28 days.

(21) Appl. No.: 09/649,406

(22) Filed: Aug. 24, 2000

(51) Int. Cl.[7] ..... A01H 5/00

(52) U.S. Cl. ..... Plt./379

(58) Field of Search ..... Plt./379

*Primary Examiner*—Bruce R. Campell
(74) *Attorney, Agent, or Firm*—Klarquist Sparkman, LLP

(57) ABSTRACT

A new and distint hybrid of *Athyrium niponicum* var. *pictum* plant characterized by exceptional silvering of the fronds and the presence of this silvering for an extended period of time.

1 Drawing Sheet

The present invention relates to a new and distinct cultivar of *Athyrium niponicum* var. *pictum,* of the family Athyriaceae, which originated as selection of several *Athyrium niponicum* var. *pictum* found in the garden of the applicant.

The new variety has been reproduced only by asexual propagation (division and tissue culture). Each of the clones exhibits identical characteristics to the original selection.

This plant is characterized by the following:

1. Exceptional silvering of the uppermost surface of its foliage.

2. This plant retains its bright silvering for an extended period of time, two months as opposed to two weeks for the species.

Asexual propagation by division and tissue culture in Canby, Oreg., shows that the foregoing characteristics and distinctions come true to type and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows *Athyrium niponicum* var. *pictum* 'Silver Falls' in a container in Canby, Oreg.

DETAILED PLANT DESCRIPTION

The following is a detailed description of the new *Athyrium niponicum* var. *pictum* selection based on observations of one and a half year old specimens grown in one-gallon containers in a cool greenhouse in Canby, Oreg. The color descriptions are all based on The Royal Horticultural Society Colour Chart.

Foliage:

*Timing*.—The plant leafs out about 1 month after the temperature is raised in a cold greenhouse (from 40 degrees F. to 50 degrees F. minimums) in the spring. Foliage dies down to the ground when the temperatures get down into the 30s to low 40s deg. F. in late fall in Canby, Oreg.

*Coloring duration*.—The foliage is lighly silvered when it first unfurls and remains highly silvered until the average high temperatures reach about 85 degrees F. Then the silvering becomes duller and reduced to the bottom half or quarter of the pinnules.

*Type*.—Compound. Sub-alternate to alternate pinnate. 15–35 pinnae below the pinnatifid tip per frond. Deciduous.

*Shape*.—Lanceolate. Segments are lanceolate to oblong or ovate.

*Length*.—To 28 cm (Whole frond excluding petiole length indicated below).

*Width*.—To 19 cm (Whole frond).

*Petiole length*.—To 25 cm.

*Margins*.—2- or 3- pinnate to pinnatifid. Segments are notched, toothed, or labed.

*Apex*.—Narrowly acute.

*Base*.—Rounded to truncate.

*Leaf texture*.—Glabrous.

*Pinnae*.—Vary from 5 to 12 cm long and from 1.5 to 2.5 cm wide.

*Pinnule number per pinnae*.—23 to 45.

*Pinnule average size*.—Varies from 0.7 cm long by 0.2 cm wide to 2.2 cm long by 0.4 cm wide.

*Petiole and rachis texture*.—Glabrous, but with chaffy scales, mainly along the base but occasionally elsewhere.

*Rachilla texture*.—Glabrous.

*Leaf arrangment*.—Clustering.

*Venation*.—Pinnate.

Size:

*Height*.—To 37 cm on a 1.5-year-old plant grown in a gallon-size pot in Canby, Oreg.

*Width*.—To 40 cm on a 1.5-year-old-plant grown in a gallon-size pot in Canby, Oreg.

Fruiting body:

*Type*.—Sporangium.

*Fertility*.—Fertile.

*Sporangium size*.—0.6 to 1.2 cm long and 0.2 to 0.5 cm wide.

*Sporangium shape*.—Contiguous, oblong, curving slightly; typical of the genus.

Habit: Creeping via rhizomes. Indefinite spread. Clustering fronds.

Disease: Have not observed any disease on plants grown commercially in Canby, Oreg.

Hardiness: USDA zones 5–9.

COLOR CHARACTERISTICS

Foliage:

*Upper surface*.—192A Greyed-Green Group over more of the frond surface than other *A. niponicum* var. *pictum* cvs.

*Upper surface, along basal portion of mid-rib*.—RHS 186C to 187A Greyed-Purple Group.

*Lower surface*.—RHS 191B Greyed-Green Group.

Petiole: Lower portion is RHS 187A Greyed-Purple Group with RHS 137A Green Group above.

Rachis: RHS 137A Green Group at the base and RHS 187A Greyed-Purple Group on top half or more.

Rachilla: RHS 187A Greyed-Purple Group.

Sorus:

*Immature*.—RHS 202A Black Group.

*Sporulating*.—RHS 166B Greyed-Orange Group.

DESCRIPTION OF PARENT PLANTS

The instant plant resulted from a selection of *Athyrium noponicum* var. *pictum. A. niponicum,* as described in *A–Z Encyclopedia of Garden Plants* by the American Horticultural Society (1996), is a "Deciduous fern with creeping red-brown rhizomes and 2- or 3-pinnate to pinnatifid, lance-shaped, silvery gray-green or mid-green fonds, to 14in (35 cm) long, with red-purple midribs . . . Segments are lance-shaped to oblong or ovate, sometimes with notched or lobed margins . . . [var. *pictum*] has fronds with purplish red stalks and silver-gray segments, sometimes flushed purple-red." 'Silver Falls' differs from *A. niponicum* var. *pictum* and named clones thereof (known to the applicant), such as 'Ursula's Red' (unpatented), in having a comparably greater overall silvery appearance and a longer period of silvering than the species.

I claim:

1. A new and distinct selection of *Athyrium niponicum* var. *pictum* plant substantially as shown and described, characterized by exceptional silvering of the fronds and the presence of this silvering for an extended period of time.

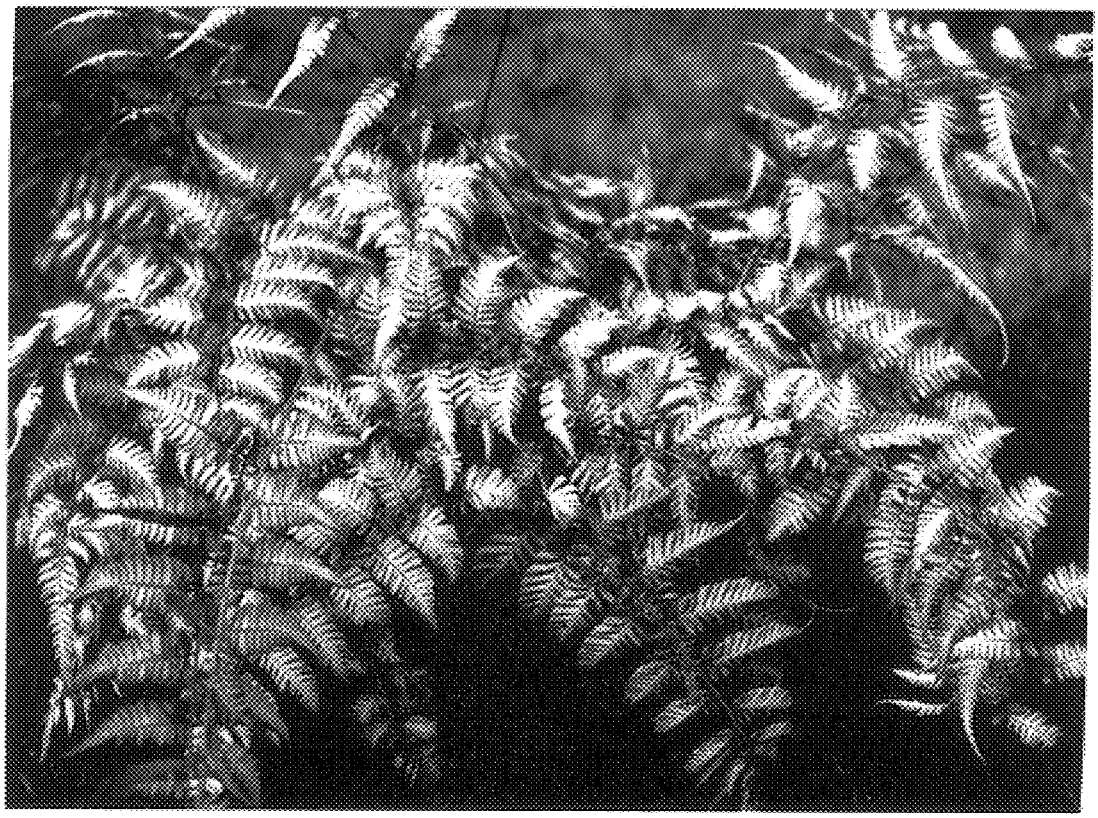

* * * * *